US012629118B2

(12) United States Patent
Braunagel

(10) Patent No.: US 12,629,118 B2
(45) Date of Patent: May 19, 2026

(54) MEDICAL IMAGING SYSTEM

(71) Applicant: KONINKLIJKE PHILIPS N.V., Eindhoven (NL)

(72) Inventor: Andre Braunagel, Garching (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 167 days.

(21) Appl. No.: 18/293,798

(22) PCT Filed: Jul. 21, 2022

(86) PCT No.: PCT/EP2022/070508
§ 371 (c)(1),
(2) Date: Jan. 31, 2024

(87) PCT Pub. No.: WO2023/011935
PCT Pub. Date: Feb. 9, 2023

(65) Prior Publication Data
US 2024/0245368 A1      Jul. 25, 2024

(30) Foreign Application Priority Data
Aug. 3, 2021    (EP) ..................................... 21189269

(51) Int. Cl.
*A61B 6/00*          (2024.01)
*A61B 6/46*          (2024.01)
(Continued)

(52) U.S. Cl.
CPC ............ *A61B 6/4405* (2013.01); *A61B 6/463* (2013.01); *A61B 6/547* (2013.01); *G06T 7/74* (2017.01);
(Continued)

(58) Field of Classification Search
CPC .... G01N 2223/1016; A61B 2090/3966; A61B 6/582; A61B 90/39; A61B 2034/2065;
(Continued)

(56) References Cited

U.S. PATENT DOCUMENTS 6,473,489 B2    10/2002  Bani-Hashemi
10,709,406 B2    7/2020  Aoshima
(Continued)

FOREIGN PATENT DOCUMENTS

EP            2220842 A1    5/2018
EP            3364214 A1 *  8/2018    ............... A61B 6/44
(Continued)

OTHER PUBLICATIONS

PCT International Search Report, International application No. PCT/EP2022/070508, Oct. 11, 2022.
(Continued)

*Primary Examiner* — Don K Wong
(74) *Attorney, Agent, or Firm* — Larry Liberchuk

(57) ABSTRACT

The present invention relates to a medical imaging system (10), comprising: an X-ray source unit (20); an X-ray detector unit (30); a sensor unit (40); a reference structure (50); and a processing unit (60)). The X-ray detector unit is configured to be placed relative to the X-ray source to acquire X-ray image data of a patient (P) positioned between the X-ray detector unit and the X-ray source unit. The reference structure is part of the X-ray detector unit or the reference structure is configured to be fixedly connected to the X-ray detector unit. An orientation of the sensor unit is known with respect to an orientation of the X-ray source unit. The sensor unit is configured to acquire a sensor image when the X-ray detector unit is placed relative to the X-ray source unit and the patient is positioned between the X-ray detector unit and the X-ray source unit, and wherein the
(Continued)

sensor image comprises image data of the reference structure. The sensor unit is configured to provide the sensor image to the processing unit. The processing unit is configured to determine a position of the X-ray detector unit with respect to a position of the X-ray source unit, and wherein the determination comprises utilization of the orientation of the sensor unit with respect to the orientation of the X-ray source unit and the image data of the reference structure.

13 Claims, 4 Drawing Sheets

(51) Int. Cl.
　　*G06T 7/73* (2017.01)
　　*A61B 90/00* (2016.01)
(52) U.S. Cl.
　　CPC ....... *A61B 90/361* (2016.02); *A61B 2090/363* (2016.02); *G06T 2207/10116* (2013.01); *G06T 2207/30004* (2013.01); *G06T 2207/30204* (2013.01)
(58) Field of Classification Search
　　CPC ...... A61B 2090/376; A61B 2090/3762; A61B 2090/3983; A61B 6/08; A61B 6/587; A61B 6/584
　　See application file for complete search history.

(56) References Cited

U.S. PATENT DOCUMENTS

| | | | |
|---|---|---|---|
| 10,835,199 | B2 | 11/2020 | Chtcheprov |
| 2003/0194056 | A1 | 10/2003 | Martin |
| 2009/0136000 | A1 | 5/2009 | Nishii |
| 2010/0239070 | A1 | 9/2010 | Mohr |
| 2014/0341356 | A1 | 11/2014 | Kurze |
| 2017/0360394 | A1 | 12/2017 | Deinlein |
| 2018/0092619 | A1 | 4/2018 | Gu |
| 2020/0281556 | A1 | 9/2020 | Wang |

FOREIGN PATENT DOCUMENTS

| | | |
|---|---|---|
| EP | 3771431 A1 | 2/2021 |
| JP | 2016034300 A | 3/2016 |

OTHER PUBLICATIONS

Clarkson M. et al., "Optical Tracking", MPHY0026: Computer Assisted Surgery and Therapy, Copyright 2019 University College London. https://mphy0026.readthedocs.io/en/latest/tracking/optical.html.

\* cited by examiner

MEDICAL IMAGING SYSTEM

FIELD OF THE INVENTION

The present invention relates to a medical imaging system, a medical imaging method, as well as to a computer program element and a computer readable medium.

BACKGROUND OF THE INVENTION

Bedside X-ray is a standard procedure that is performed everywhere where the patient cannot stand upright for a conventional X-ray radiography examination. An example of a bedside X-ray procedure is for chest examinations, since pulmonary disorders are quite common in patients who are immobile. An X-ray detector unit is placed behind the patient lying on the bed, thus typically between the patient and the mattress, and where the mattress could be hinged in the middle thereby inclining the patient and therefore the X-ray detector need not be horizontal. An X-ray source is then positioned in front of the patient and an X-ray image or radiogram is acquired.

One of the problems that is associated with an optimal acquisition of bedside X-rays with such a mobile X-ray system is the correct positioning of the field of view. In particular, as discussed above the X-ray detector is positioned behind the patient's back and the X-ray source or tube has to be positioned and its collimation adapted in such a manner that the chest of the patient is properly imaged. Misalignment of the X-ray tube with the detector leads to cut-off images that hamper proper image reading. A proper alignment between the detector and the X-ray tube/source is difficult to achieve, since the exact position of the detector is typically not visible behind the patient's back. Hence, a significant number of X-ray images have suboptimal patient positioning, which in its turn leads to missed diagnosis and suboptimal workflow as some images have to be retaken. An example of a cut-off image is shown in FIG. 1.

There is a need to resolve this issue.

SUMMARY OF THE INVENTION

It would be advantageous to have an improved medical imaging system for acquiring bedside X-ray images of patients, that provides utility to mobile medical imaging systems. The object of the present invention is solved with the subject matter of the independent claims, wherein further embodiments are incorporated in the dependent claims. It should be noted that the following described aspects and examples of the invention apply to the medical imaging system, and also to the medical imaging method as well as to the computer program element and the computer readable medium.

In a first aspect, there is provided a medical imaging system, comprising:

an X-ray source unit;
an X-ray detector unit;
a sensor unit;
a reference structure; and
a processing unit.

The X-ray detector unit is configured to be placed relative to the X-ray source to acquire X-ray image data of a patient (P) positioned between the X-ray detector unit and the X-ray source unit. The reference structure is part of the X-ray detector unit or the reference structure is configured to be fixedly connected to the X-ray detector unit. An orientation of the sensor unit is known with respect to an orientation of the X-ray source unit. The sensor unit is configured to acquire a sensor image when the X-ray detector unit is placed relative to the X-ray source unit and the patient is positioned between the X-ray detector unit and the X-ray source unit, and the sensor image comprises image data of the reference structure. The sensor unit is configured to provide the sensor image to the processing unit. The processing unit is configured to determine a position of the X-ray detector unit with respect to a position of the X-ray source unit. The determination comprises utilization of the orientation of the sensor unit with respect to the orientation of the X-ray source unit and the image data of the reference structure.

Thus, the system is configured such that when the detector unit is behind a patient, a reference structure that is a part of the detector unit or that has been fixedly attached or connected to the detector unit can be imaged. The processing unit can then determine the position and orientation of the sensor unit with respect to the detector unit through interpretation of the imaged reference structure. Then, because the orientation of the sensor unit with respect to the source unit is known, the processing unit can determine the position and orientation of the detector unit with respect to the source unit. It can then be determined if the detector unit is correctly positioned, or if it is off-centered and/or twisted or tilted, and also the applied collimation can be checked with respect to the detector position.

In an example, the processing unit is configured to determine a required movement of the X-ray source unit on the basis of the determined position of the X-ray detector unit with respect to the position of the X-ray source unit.

In this manner, an automatic or semi-automatic solution can be provided. Thus, the required movement can be in the form of a required movement provided to an operator, who then moves the source unit. However, the source unit can be mounted in a mechanical movement system providing for at least some movement of the source unit. Thus, the processing unit can determine how the source unit needs to be moved and can then control the movement of the source unit to move it to a new required and optimized position with respect to the detector unit.

Also, it is normally required to have a pre-defined or required source to image distance (SID) for proper imaging results, and the system enables it to be checked if the distance between the source and the detector are suitable. Thus, the required movement can be a translational movement sideways and/or a movement forwards backwards.

In an example, the system comprises a visual display unit (VDU), and the sensor image comprises image data of the patient. The processing unit is configured to project the image data of the patient onto the VDU with respect to the position of the X-ray source unit and the processing unit is configured to display on the VDU a representation of the position of the X-ray detector unit with respect to the position of the X-ray source unit.

In other words, an image of the patient is displayed on a VDU as if the X-ray source had acquired the image of the patient and at the same time a representation of the position of the detector, such as an outline of the outer extent of the detector area is also displayed on the VDU. In this way an operator can quickly and effectively see if the detector is correctly aligned with respect to the X-ray source and whether the patient is correctly aligned with respect to the X-ray source and/or the detector.

In an example, the reference structure comprises a handle of the X-ray detector unit.

In an example, the reference structure comprises a structure extending laterally from an edge of the X-ray detector unit.

In an example, the reference structure comprises one or more markers.

In an example, the one or more markers extend perpendicularly to the structure extending laterally from the edge of the X-ray detector unit.

In an example, the reference structure comprises three markers.

In an example, the one or more markers comprises a plurality of markers and wherein a first marker is oriented perpendicularly to a second marker.

In an example, the first marker is oriented perpendicularly to the third marker.

Thus, the reference structure is in effect a calibration structure, and image data of the reference structure enables the distance to and orientation of the reference structure to be determined, from which the distance to and orientation of the detector can be determined because the reference structure is at a known location and orientation with respect to the detector itself. Then, as detailed above this can be used to determine the relative positions of the X-ray source unit and X-ray detector unit enabling it to be determined if they are correctly aligned one with the other.

In an example, the sensor unit is integrated with the X-ray source unit.

In this manner, a simple combined source/sensor unit is provided. However, the sensor unit and source unit need not be in a combined unit.

In an example, the sensor image comprises image data of the patient. The processing unit is configured to determine a collimation of the X-ray source unit comprising utilization of the orientation of the sensor unit with respect to the orientation of the X-ray source unit and the image data of the patient.

In this manner, not only can it be determined if the x-ray source is correctly aligned with the X-ray detector it can be determined if the patient is correctly aligned with respect to the X-ray source and its collimation adjusted if required.

In an example, the processing unit is configured to determine a required movement of the X-ray source unit on the basis of the determined collimation of the X-ray source unit.

In an example, the processing unit is configured to determine a required movement of the X-ray detector unit on the basis of the determined collimation of the X-ray source unit.

Thus, the new collimation could then lead to the X-ray source unit not then being correctly aligned with respect to the X-ray detector unit. However, now the X-ray source and/or the X-ray detector unit can then be moved with respect to each other and indeed with respect to the patient, and indeed if necessary the patient could be moved, in order to provide for correct exposure. This can lead to a further slight adjustment in the required collimation of the X-ray source and to further movements of the X-ray source/X-ray detector, which is facilitated by the new system. The collimation and movement of the X-ray source unit can be fully automated and controlled by the processing unit, or information can be provided to an operator to adjust the collimation and move the source etc.

In a second aspect, there is provided a medical imaging method, comprising:

a) placing an X-ray source unit relative to an X-ray detector unit to acquire X-ray image data of a patient positioned between the X-ray detector unit and the X-ray source unit, and wherein a reference structure is part of the X-ray detector unit or the reference structure is fixedly connected to the X-ray detector unit;

b) acquiring a sensor image with a sensor unit, wherein the sensor image comprises image data of the reference structure, and wherein an orientation of the sensor unit is known with respect to an orientation of the X-ray source unit;

c) providing the sensor image to a processing unit; and d) determining by the processing unit a position of the X-ray detector unit with respect to a position of the X-ray source unit, and wherein the determining comprises utilizing the orientation of the sensor unit with respect to the orientation of the X-ray source unit and the image data of the reference structure.

According to another aspect, there is provided a computer program element controlling one or more of the systems as previously described which, if the computer program element is executed by a processor, is adapted to perform the method as previously described.

According to another aspect, there is provided a computer readable medium having stored computer element as previously described.

The computer program element can for example be a software program but can also be a FPGA, a PLD or any other appropriate digital means.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawing.

DETAILED DESCRIPTION OF EMBODIMENTS

Figure 1:
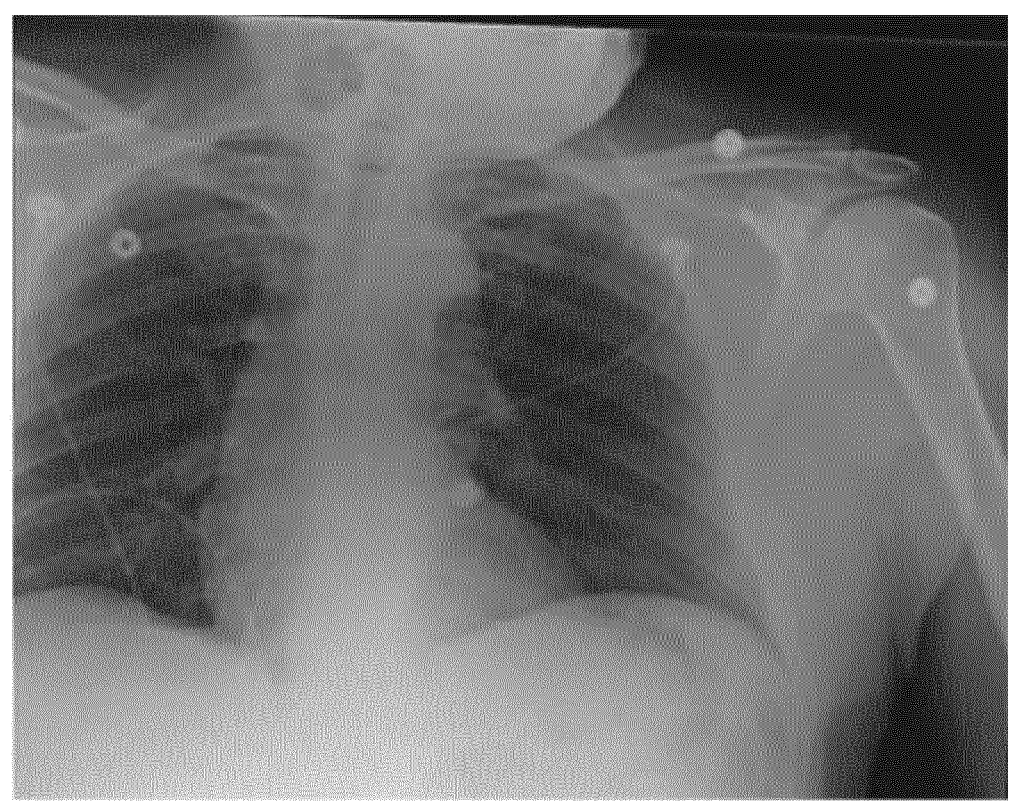
FIG. 1 shows an exemplar bedside chest X-ray showing an improper detector positioning and a cut-off lung.
Figure 2:
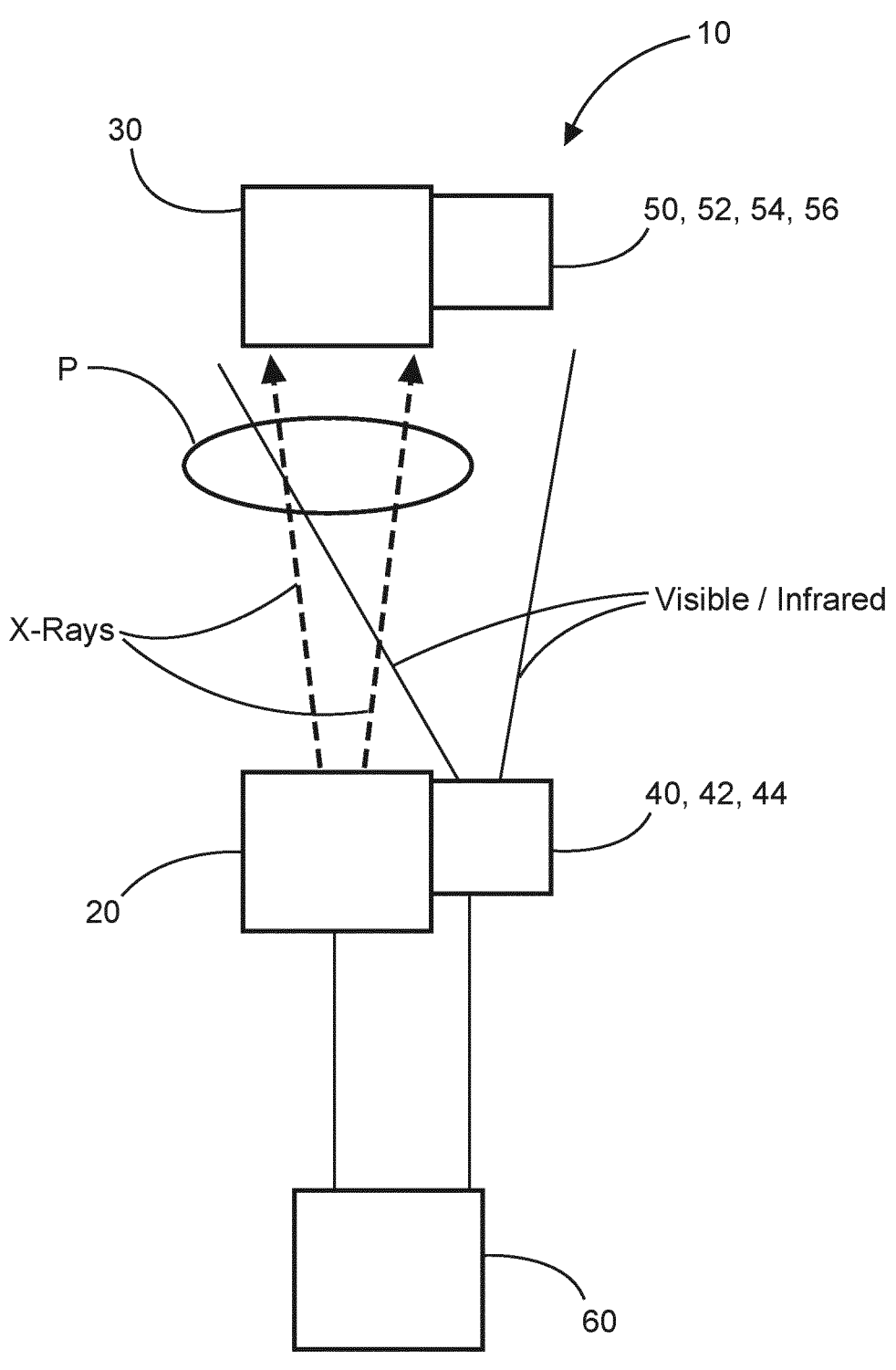
FIG. 2 shows a medical imaging system.

FIG. 2 shows a schematic example of a medical imaging system 10. The medical imaging system comprises an X-ray source unit 20, an X-ray detector unit 30, a sensor unit 40, a reference structure 50, and a processing unit 60. The X-ray detector unit 30 is configured to be placed relative to the X-ray source unit 20 to acquire X-ray image data of a patient (P) positioned between the X-ray detector unit 30 and the X-ray source unit 20. The reference structure 50 is part of the X-ray detector unit 30 or the reference structure 50 is configured to be fixedly connected to the X-ray detector unit 30. An orientation of the sensor unit 40 is known with respect to an orientation of the X-ray source unit 20. The sensor unit 40 is configured to acquire a sensor image when the X-ray detector unit 30 is placed relative to the X-ray source unit 20 and the patient is positioned between the X-ray detector unit 30 and the X-ray source unit 20, and the sensor image comprises image data of the reference structure 50. The sensor unit 40 is configured to provide the sensor image to the processing unit 60. The processing unit 60 is configured to determine a position of the X-ray detector unit 30 with respect to a position of the X-ray source unit 20. The determination of the position of the X-ray detector unit 30 with respect to the position of the X-ray source unit 20 comprises utilization of the orientation of the sensor unit 40 with respect to the orientation of the X-ray source unit 20 and the image data of the reference structure 50.

In an example, the medical imaging system 10 is a mobile medical imaging system.

In an example, the sensor unit 40 is a camera unit and the sensor image is a camera image.

In an example, the camera unit is a 3D camera unit. Thus, the camera unit can have two cameras 42, 44 and the camera image is then an image generated from the two images of the 3D camera, providing an efficient means to determine the distance to and orientation of the reference structure 50 with respect to the camera unit and hence the position and orientation of the X-ray detector unit 30 with respect to the camera unit, and as detailed above then translate this into the position and orientation of the X-ray detector unit 30 with respect to the X-ray source unit 20. However, the camera unit need not be a 3D camera and a 2D image can be utilized.

In an example, the reference structure 50 has for example a stalk 54 of a known length, or segments of known length, then image data of this structure can be used to determine a distance of the reference structure 50 from the camera unit. Then, parts 56 of the reference structure 50 can extend in a known way from a stalk and image data of these parts can be used to determine a rotational aspect of the reference structure 50 to the camera unit. Thus, then a distance and orientation of the reference structure 50 and hence the distance and orientation of the X-ray detector unit 30 from the camera unit can be determined on the basis of this 2D image, and then as detailed above the position and orientation of the X-ray detector unit 30 with respect to the X-ray source unit 20 can then be determined.

In an example, the camera unit comprises one or more radiation sources 46, 48. In an example, the one or more radiation sources are infrared radiation sources.

Thus, the system can operate in all light conditions.

In an example, the reference structure 50 has reflector segments. In an example the reflector segments are designed to reflect radiation emitted by the one or more radiation sources.

In an example, the sensor unit 40 is a LIDAR unit, and the sensor image is an image constructed from laser range information.

In an example, the sensor unit 40 is a radar unit, and the sensor image is a radar range constructed image.

According to an example, the processing unit 60 is configured to determine a required movement of the X-ray source unit 20 on the basis of the determined position of the X-ray detector unit 30 with respect to the position of the X-ray source unit 20.

In an example, the processing unit 60 is configured to determine a required movement of the X-ray detector unit 30 on the basis of the determined position of the X-ray detector unit 30 with respect to the position of the X-ray source unit 20.

According to an example, the system comprises a visual display unit (VDU). The sensor image can comprise image data of the patient, and the processing unit 60 is configured to project the image data of the patient onto the VDU with respect to the position of the X-ray source unit 20 and the processing unit 60 is configured to display on the VDU a representation of the position of the X-ray detector unit 30 with respect to the position of the X-ray source unit 20 and also with respect to the patient.

In an example, the processing unit 60 is configured to project a field of view of the X-ray source unit 20 onto the VDU.

According to an example, the reference structure 50 comprises a handle 52 of the X-ray detector unit 30.

According to an example, the reference structure 50 comprises a structure 54, 56 extending laterally from an edge of the X-ray detector unit 30.

In an example, the structure 54, 56 extending laterally from an edge of the X-ray detector unit comprises a stalk 54.

In an example, the stalk 54 has known length and/or segments of known length, and the determination of the position of the X-ray detector unit 30 with respect to the position of the X-ray source unit 20 can comprise utilization of the known length of the stalk 54 and/or known length of the segments of the stalk 54.

According to an example, the reference structure 50 comprises one or more markers 56.

In an example, the one or more markers 56 are located at known positions and orientations with respect to the stalk 54 of the reference structure 50, and the determination of the position of the X-ray detector unit 30 with respect to the position of the X-ray source unit 20 can comprise utilization of the known positions and orientations of the one or more markers 56 with respect to the stalk 54 of the reference structure 50.

According to an example, the one or more markers 56 extend perpendicularly to the structure extending laterally from the edge of the X-ray detector unit 30.

In an example, the one or more markers 56 extend a known length perpendicularly to the structure extending laterally from the edge of the X-ray detector unit 30 (such as the stalk 54). The determination of the position of the X-ray detector unit 30 with respect to the position of the X-ray source unit 20 can then comprise utilization of the known length of the one or more markers 56 that extend perpendicularly to the structure extending laterally from the edge of the X-ray detector unit 30.

According to an example, the reference structure 50 comprises three markers 56.

According to an example, the one or more markers 56 comprises a plurality of markers and wherein a first marker is oriented perpendicularly to a second marker.

According to an example, the first marker is oriented perpendicularly to the third marker.

According to an example, the sensor unit 40 is integrated with the X-ray source unit 20.

According to an example, the sensor image comprises image data of the patient. The processing unit 60 is configured to determine a collimation of the X-ray source unit 20 comprising utilization of the orientation of the sensor unit 40 with respect to the orientation of the X-ray source unit 20 and the image data of the patient.

According to an example, the processing unit 60 is configured to determine a required movement of the X-ray source unit 20 on the basis of the determined collimation of the X-ray source unit 20. Additionally, or alternatively, the processing unit 60 is configured to determine a required movement of the X-ray detector unit 30 on the basis of the determined collimation of the X-ray source unit 20.

Figure 3:
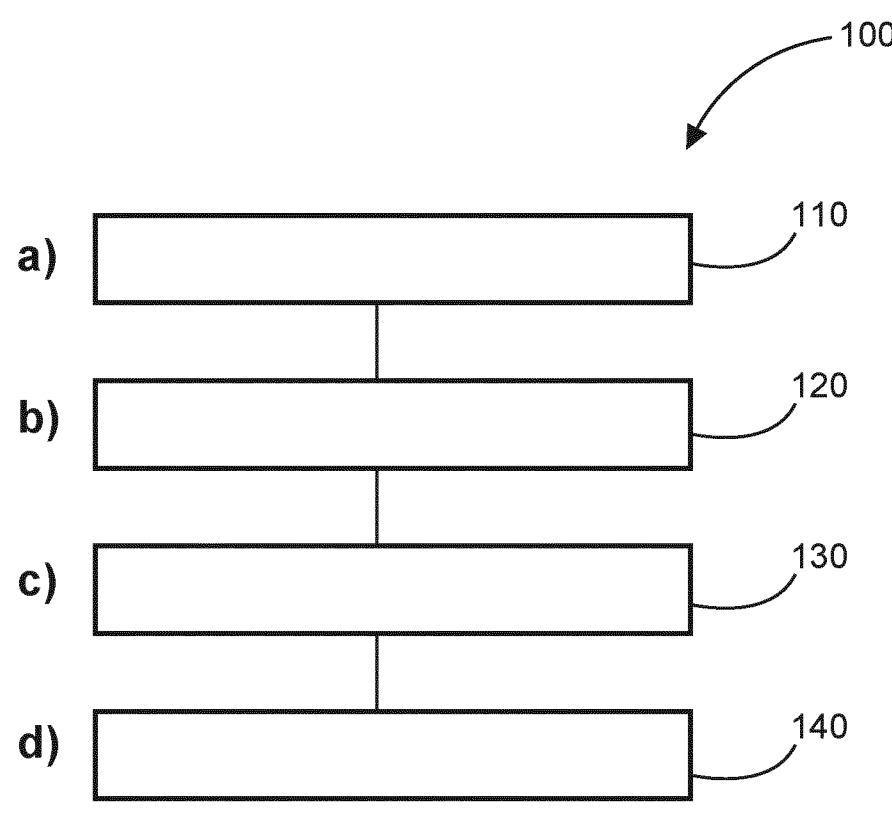
FIG. 3 shows a medical imaging method.

FIG. 3 shows an example of a medical imaging method 100 in its basic steps. The method comprise:

in a placing step 110, also referred to as step a), placing an X-ray source unit 20 relative to an X-ray detector unit 30 to acquire X-ray image data of a patient positioned between the X-ray detector unit 30 and the X-ray source unit 20, and wherein a reference structure 50 is part of the X-ray detector unit 30 or the reference structure 50 is fixedly connected to the X-ray detector unit 30;

in an acquiring step 120, also referred to as step b), acquiring a sensor image with a sensor unit 40, wherein the sensor image comprises image data of the reference structure 50, and wherein an orientation of the sensor unit 40 is known with respect to an orientation of the X-ray source unit 20;

in a providing step 130, also referred to as step c), providing the sensor image to a processing unit 60; and in a determining step 140, also referred to as step d), determining by the processing unit 60 a position of the X-ray detector unit 30 with respect to a position of the X-ray source unit 20, and wherein the determining comprises utilizing the orientation of the sensor unit 40 with respect to the orientation of the X-ray source unit 20 and the image data of the reference structure 50.

In an example, the medical imaging system is a mobile medical imaging system.

In an example, the sensor unit 40 is a camera unit and the sensor image is a camera image.

In an example, the camera unit is a 3D camera unit.

In an example, the camera unit comprises one or more radiation sources 46, 48. In an example, the one or more radiation sources are infrared radiation sources.

In an example, the reference structure 50 has reflector segments. In an example the reflector segments are designed to reflect radiation emitted by the one or more radiation sources.

In an example, the sensor unit 40 is a LIDAR unit, and the sensor image is an image constructed from laser range information.

In an example, the sensor unit 40 is a radar unit, and the sensor image is a radar range constructed image.

In an example, the method comprises determining by the processing unit 60 a required movement of the X-ray source unit 20 on the basis of the determined position of the X-ray detector unit 30 with respect to the position of the X-ray source unit 20.

In an example, the method comprises determining by the processing unit 60 a required movement of the X-ray detector unit 30 on the basis of the determined position of the X-ray detector unit 30 with respect to the position of the X-ray source unit 20.

In an example, the reference structure 50 comprises a handle of the X-ray detector unit.

In an example, the sensor image comprises image data of the patient, and the method comprises projecting by the processing unit 60 the image data of the patient onto a visual display unit (VDU) with respect to the position of the X-ray source unit 20 and displaying by the processing unit 60 on the VDU a representation of the position of the X-ray detector unit 30 with respect to the position of the X-ray source unit 20.

In an example, the method comprises projecting by processing unit 60 a field of view of the X-ray source unit 20 onto the VDU.

In an example, the reference structure 50 comprises a structure 54, 56 extending laterally from an edge of the X-ray detector unit 30.

In an example, the reference structure 50 comprises one or more markers 56.

In an example, the one or more markers 56 extend perpendicularly to the structure extending laterally from the edge of the X-ray detector unit 30.

In an example, the reference structure 50 comprises three markers.

In an example, the one or more markers 56 comprises a plurality of markers and wherein a first marker is oriented perpendicularly to a second marker.

In an example, the first marker is oriented perpendicularly to the third marker.

In an example, the sensor unit 40 is integrated with the X-ray source unit 20.

In an example, the sensor image comprises image data of the patient, and the method comprises determining by the processing unit 60 a collimation of the X-ray source unit 20. This determining can comprise utilizing the orientation of the sensor unit 40 with respect to the orientation of the X-ray source unit 20 and the image data of the patient.

In an example, the method comprises determining by the processing unit 60 a required movement of the X-ray source unit 20 on the basis of the determined collimation of the X-ray source unit 20.

In an example, the method comprises determining by the processing unit 60 a required movement of the X-ray detector unit 30 on the basis of the determined collimation of the X-ray source unit 20.

Figure 4:
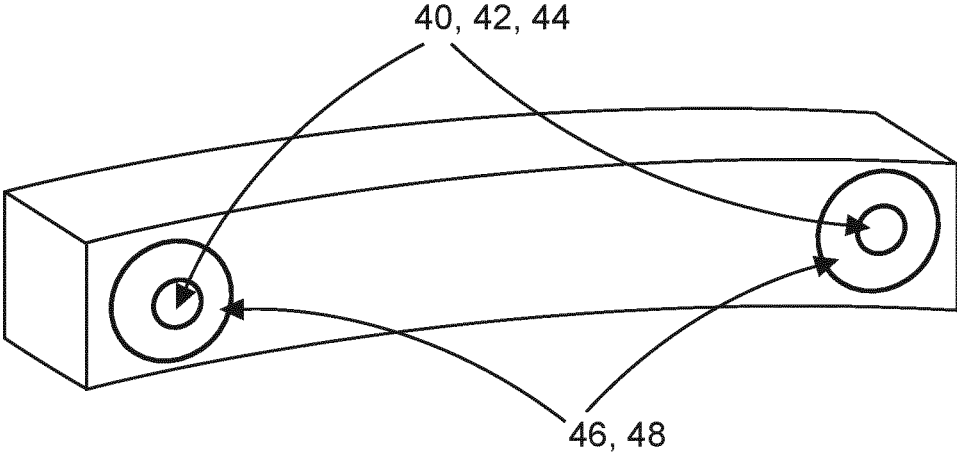
FIG. 4 shows an exemplar optical tracking system or camera unit.
Figure 5:
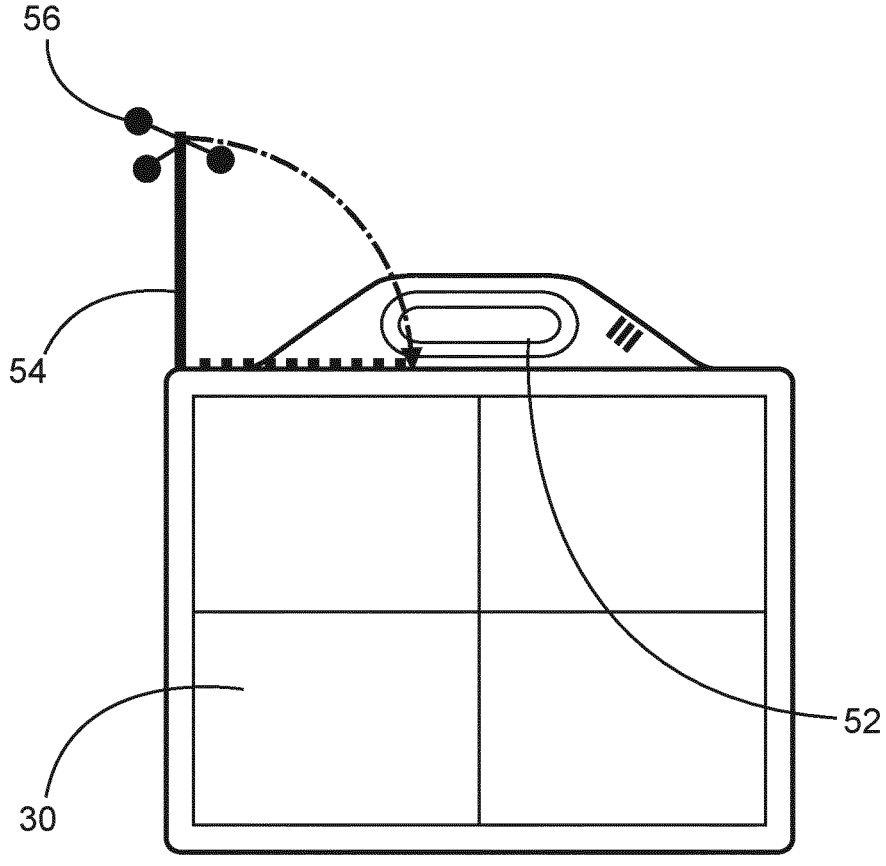
FIG. 5 shows a detector unit with exemplar reference structures.

The medical imaging system and medical imaging method are further explained in specific detail, where reference is made to FIGS. 4-5. The medical imaging system and method are described with respect to a mobile imaging system and method, however the system and method also apply to a "normal" X-ray tube that is used in order to acquire an X-ray image of a patient lying in bed with a portable detector that is placed behind the patient. Also, the medical imaging system and method are described with respect to a sensor unit in the form of a 3D camera unit or system, but a 2D camera, radar sensor or lidar sensor, or other range sensor could be utilized.

In developing the new system and method it was realized that optical tracking systems could be utilized, along with a modified detector housing or unit, in order to improve the acquisition of bedside X-rays using mobile X-ray systems. Such optical tracking systems are based for example on 3D cameras, here called a camera unit. A new technique was developed, using such an optical tracking system, to improve the acquisition of bedside X-rays using mobile X-ray systems by enabling the position of the X-ray tube, also called an X-ray source unit, to be determined with respect to the X-ray detector unit. It can then be established if the components of the system are positioned correctly with respect to each other and that the correct field of view of the patient will be captured, or if adjustment is required. Reference is made above to an optical tracking system, however it was established that an appropriate radar based system or LIDAR system can be utilized.

FIG. 4 shows an example of a sensor unit 40 in the form of a camera unit and indeed in the form of a 3D camera. It is to be noted that although 3D imagery is acquired. 2D imagery can be utilized with an appropriate reference structure 50, 52, 54, 56—shown in FIG. 5.

Continuing with FIG. 4, the optical tracking system or camera unit 40 typically consists of two light sources 46, 48 and two cameras 42, 44 that are positioned at a certain distance from each other, resulting in a 3D camera. The emitted light can be both in the visible or in the infrared range or indeed in both of these parts of the spectrum. A commercially available optical tracking system is provided for example by Polaris Spectra.

The camera unit 40 of FIG. 4 is utilized with a modified detector unit 30 of FIG. 5. The modified detector unit 30 has a reference structure 50 with for example markers 56 of a known geometry positioned on the end of a stalk 54, or the reference structure 50 can be in the form of an enlarged handle 52 of the detector unit 30. The reference structure 50 has a known geometrical arrangement with respect to the detector unit 30 structure, and can be an integral part of the detector unit 30 or be attachable to the detector unit 30. The reference structure 50, or at least the markers 56, must be visible to the camera unit 40. Optical tracking is then utilized to localize the markers 56 in space, with for example 0.25 mm accuracy. Triangulation for example is used in this location determination in order to determine the 3D location of each marker 56 and this is then matched to the known geometry of the markers 56 to determine the pose of the reference structure 50 with respect to a coordinate system of the camera unit 40. As the manner in which the reference structure 50 is positioned relative to the detector unit 30 is known, the position and pose, or orientation, of the detector unit 30 with respect to the camera unit 40 is then known.

As the camera unit's position and pose is known with respect to the X-ray source unit's, which is most conveniently achieved by having both mounted fixedly in the same unit, the position and pose of the detector unit 30 with respect to the source unit 20 can be determined, enabling it to be determined if the field of view will correctly fill the required part of the detector.

Thus in a specific example the optical tracking system or camera unit 40 is in effect integrated into the tube-head or X-ray source unit 20 of a mobile system and a processing unit 60 can control movement of the collimation shutters, and indeed the X-ray source unit 20 can be on a mobile motorized gantry allowing for the X-ray source unit 20 to be moved right/left/up/down and even tilted as required under the control of the processing unit 60. Currently, as discussed above the exact position of the detector behind the patient is difficult to estimate as the detector is completely hidden behind the patient.

As shown in FIG. 5, in addition to having a source unit 20 operating with a camera unit 40, a modified detector unit 30 is utilized. The detector unit 30, which here includes the housing of the detector, has been adapted or has a connected part such that a reference structure part 50 is visible to the camera unit even after placing the detector unit behind the patient. As discussed above the reference structure can be in the form of an enlarged handle 52, or a structure in the form of a stalk 54 with markers 56 at the end. Conveniently, the stalk 54 and markers 56 can be designed to fold into the main body of the detector unit 30.

Thus, this visible reference structure 50, 52, 54, 56, that is used to calculate the position of the detector unit 30 can be for example a stalk 54 of known length at the end of which are markers 56 of known geometrical arrangement. This can be permanently positioned, or be connected and disconnected as required, but being positioned in a known position, or fold inwards to the main body of the detector unit 30. Thus, at the tip of this reference structure 50 the markers 56 in the form of reflectors enable position tracking to be carried out to enable the position and pose of the reference structure 50 and hence of the detector unit 30 to be calculated with respect to the camera unit 40 and thence with respect to the source unit 20. Alternatively, the handle 52 of the detector unit 30 could be adapted/enlarged, so that it is visible after placement and the reflective spheres can also if necessary be attached to the detector handle 52 in order to form a reference structure 50. Thus, after the detector unit 30 has been placed behind the patient the optical tracking system that consists of a 3D camera 40, 42, 44 and light emitters 46, 48 can find and locate the visible reference structure 50 and due to the rigid connection calculate the exact position of the detector unit 30.

By motorizing for example the column with the X-ray tube or X-ray source unit 20, the positioning of the X-ray tube can be automatically adjusted in such a manner in order to ensure that the detector within the detector unit 30 is optimally illuminated.

Furthermore, the 3D camera unit 40 and optical tracking can be further used to determine and apply the optimal collimation for the X-ray source 20. To achieve this, the 3D camera unit 40 detects landmarks on the human thorax, that can for example be markers placed on the patient's body, and calculate the optimal collimation. Therefore, the X-ray shutters or collimators can be automatically adapted in order to achieve the calculated optimal collimation.

Thus, this enables a completely new manner in which to provide for optimized and automatic field of view positioning, where the detector is optimally illuminated with X-rays and at the same time the required part of the patient is illuminated with X-rays, and all in a mobile medical imaging system that can be utilized for bedside radiogram acquisition. Thus, the new approach has the advantage that it not only allows to track the position of the detector behind the patient but also to allow for an optimal collimation.

The new approach can be summarized as following:

Place the detector unit 30 behind the patient

Ensure that either the handle 52 as a reference structure 50, or a specific reference structure 54, 56 is visible behind the patient The 3D camera 40 detects the detector handle 52 or the reference structure 54, 56 and calculates the position of the detector unit 30 and the detector itself Based on the calculated position of the detector unit 30, the X-ray source unit/tube 20 is either automatically positioned in order to properly illuminate the detector if the column is motorized or guidance is provided to the user as to how to position the X-ray tube 20 in order to ensure proper illumination of the detector The 3D camera 40 detects the landmarks of the patient and choses the proper collimation and checks if the proper collimation is covered by the current detector position. In the situation where the current detector position is not suitable to cover the field of view, a notice is provided to the user to adapt the detector position and the process is repeated again from step 1)—it is to be noted that the detector unit 30 can also be moved automatically in mounted in an appropriate motorized outer housing.

Thus, the described method ensures proper choice of field of view and improved the clinical workflow.

In another exemplary embodiment, a computer program or computer program element is provided that is characterized by being configured to execute the method steps of the method according to one of the preceding embodiments, on an appropriate system.

The computer program element might therefore be stored on a computer unit, which might also be part of an embodiment. This computing unit may be configured to perform or induce performing of the steps of the method described previously. Moreover, it may be configured to operate the components of the above described apparatus and/or system. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A medical imaging system, comprising:
an X-ray source;
an X-ray detector configured to be placed relative to the X-ray source to acquire X-ray image data of a patient positioned between the X-ray detector and the X-ray source;
a sensor configured to acquire a sensor image when the X-ray detector is placed relative to the X-ray source and the patient is positioned between the X-ray detector and the X-ray source, wherein an orientation of the sensor is known with respect to an orientation of the X-ray source;
a reference structure being a part of the X-ray detector or configured to be fixedly connected to the X-ray detector, wherein the sensor image comprises image data of the reference structure and image data of the patient; and
a processor configured to determine 1) a position of the X-ray detector with respect to a position of the X-ray source, and 2) a collimation of the X-ray source, and wherein the determination comprises utilization of the orientation of the sensor with respect to the orientation of the X-ray source and the image data of the reference structure.

2. The system according to claim 1, wherein the processor is configured to determine a required movement of the X-ray source based on the determined position of the X-ray detector with respect to the position of the X-ray source.

3. The system according to claim 1, wherein the reference structure comprises a handle of the X-ray detector.

4. The system according to claim 1, wherein the reference structure comprises a structure extending laterally from an edge of the X-ray detector.

5. The system according to claim 4, wherein the reference structure comprises one or more markers.

6. The system according to claim 5, wherein the one or more markers extend perpendicularly to the structure extending laterally from the edge of the X-ray detector.

7. The system according to claim 5, wherein the reference structure comprises three markers.

8. The system according to claim 7, wherein the one or more markers comprises a plurality of markers, and wherein a first marker is oriented perpendicularly to a second marker.

9. The system according to claim 8, wherein the first marker is oriented perpendicularly to the third marker.

10. The system according to claim 1, wherein the sensor is integrated with the X-ray source.

11. The system according to claim 1, wherein the processor is configured to determine a required movement of the X-ray source based on the determined collimation of the X-ray source; and/or wherein the processor is configured to determine a required movement of the X-ray detector based on the determined collimation of the X-ray source.

12. A medical imaging method, comprising:
placing an X-ray source relative to an X-ray detector to acquire X-ray image data of a patient positioned between the X-ray detector and the X-ray source, and wherein a reference structure is part of the X-ray detector or the reference structure is fixedly connected to the X-ray detector;
acquiring a sensor image with a sensor, wherein the sensor image comprises image data of the reference structure and image data of the patient, and wherein an orientation of the sensor is known with respect to an orientation of the X-ray source;
providing the sensor image to a processor;

determining by the processor a position of the X-ray detector with respect to a position of the X-ray source, and wherein the determining comprises utilizing the orientation of the sensor with respect to the orientation of the X-ray source and the image data of the reference structure;

displaying the image data of the patient with respect to the position of the X-ray source; and displaying a representation of the position of the X-ray detector with respect to the position of the X-ray source.

13. A non-transitory computer-readable medium for storing executable instructions, which cause a medical imaging method to be performed, the method comprising:

placing an X-ray source relative to an X-ray detector to acquire X-ray image data of a patient positioned between the X-ray detector and the X-ray source, and wherein a reference structure is part of the X-ray detector or the reference structure is fixedly connected to the X-ray detector;

acquiring a sensor image with a sensor, wherein the sensor image comprises image data of the reference structure and image data of the patient, and wherein an orientation of the sensor is known with respect to an orientation of the X-ray source;

providing the sensor image to a processor; and determining by the processor a position of the X-ray detector with respect to a position of the X-ray source, and wherein the determining comprises utilizing the orientation of the sensor with respect to the orientation of the X-ray source and the image data of the reference structure;

displaying the image data of the patient with respect to the position of the X-ray source; and displaying a representation of the position of the X-ray detector with respect to the position of the X-ray source.

* * * * *